United States Patent [19]

Kennedy

[11] Patent Number: 4,677,841

[45] Date of Patent: Jul. 7, 1987

[54] METHOD AND APPARATUS FOR MEASURING THE RELATIVE DENSITY OF GASES

[75] Inventor: Lyn R. Kennedy, Dallas, Tex.

[73] Assignee: Precision Measurement, Inc., Duncanville, Tex.

[21] Appl. No.: 836,860

[22] Filed: Mar. 6, 1986

Related U.S. Application Data

[63] Continuation of Ser. No. 597,176, Apr. 5, 1984, abandoned.

[51] Int. Cl.$^4$ .......................... G01N 9/26; G01N 9/32
[52] U.S. Cl. ...................................................... 73/30
[58] Field of Search .................. 73/30, 23, 37.5, 37.6, 73/37.7, 1 G, 861

[56] References Cited

U.S. PATENT DOCUMENTS

| | | |
|---|---|---|
| 527,397 | 10/1894 | Arndt . |
| 2,023,164 | 12/1935 | Cady . |
| 2,286,864 | 6/1942 | Luhrs ........................ 73/30 |
| 2,662,394 | 12/1953 | McMahon . |
| 2,670,625 | 3/1954 | Snavely . |
| 2,703,494 | 3/1955 | Carney ....................... 73/30 |
| 2,724,962 | 11/1955 | McMahon . |
| 2,838,927 | 6/1958 | Gray ........................... 73/30 |
| 3,082,618 | 3/1963 | Nerheim . |
| 3,145,564 | 8/1964 | Poole et al. ................ 73/30 |
| 3,339,399 | 9/1967 | Hubbard et al. ........... 73/30 |
| 3,350,918 | 11/1967 | Berling . |
| 3,488,649 | 1/1970 | Lee . |
| 3,544,276 | 12/1970 | Merwitz, Sr. . |
| 3,545,255 | 12/1970 | Levy et al. . |
| 3,572,094 | 3/1971 | Banks ......................... 73/30 |
| 3,693,403 | 9/1972 | Paul . |
| 3,701,280 | 10/1972 | Stroman .................... 73/30 |
| 3,916,672 | 11/1975 | Stansfeld . |
| 4,033,171 | 7/1977 | Karas et al. ............... 73/23.1 |
| 4,100,789 | 7/1978 | Joyce .......................... 73/23 |
| 4,170,892 | 10/1979 | Bailitis . |
| 4,175,423 | 11/1979 | Braun et al. ............... 73/30 |
| 4,194,385 | 3/1980 | November .................. 73/30 |
| 4,285,245 | 8/1981 | Kennedy .................... 73/861 |
| 4,384,472 | 5/1983 | Tournier ..................... 73/30 |

OTHER PUBLICATIONS

*Perry's Chemical Engineers' Handbook*, Sixth Ed., McGraw Hill, Sec. 5, pp. 14–16, 1984.

Primary Examiner—Stephen A. Kreitman
Attorney, Agent, or Firm—Thomas L. Cantrell; Stanley R. Moore

[57] ABSTRACT

Gas is vented through a very small orifice or pore with substantially stable pressures before and after the orifice. The orifice is designed so that the expansion through it is similar to a Joule-Thompson expansion of the gas. With ideal gas, this occurs isothermally. The flow through this orifice is determined for a selected pressure drop across it and the square of this flow is inversely proportional to the relative density. With real gases there is a slight error introduced due to a supercompressibility of the gas, but this is offset by an error in the opposite direction believed to be due to the Joule-Thompson cooling of the gas as it passes through the orifice. Substantially exact error cancellation is obtained within a predetermined operating range of the pressure drop across the orifice for a given orifice diameter.

16 Claims, 1 Drawing Figure

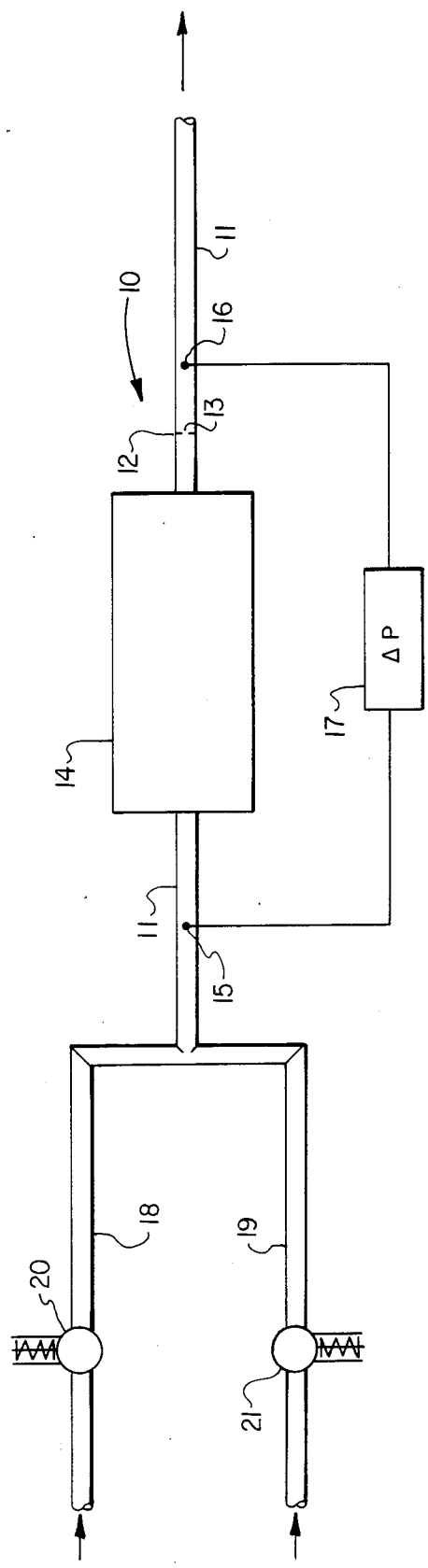

METHOD AND APPARATUS FOR MEASURING THE RELATIVE DENSITY OF GASES

This is a continuation of application Ser. No. 597,176, filed Apr. 5, 1984, now abandoned.

BACKGROUND OF THE INVENTION

A common method of metering gases involves passing the gas through a flow tube or orifice plate and measuring the pressure drop produced. Flow depends not only on the pressure drop, however, but also on the relative density of the gas. The latter must be measured independently in order to calibrate the meter and obtain accurate flow measurements for gases of varying composition. It is also often necessary to convert volumetric flow measurements of gases to mass flow or vice versa. Either of these conversions must use the relative density of the gas.

With gaseous fuels it is sometimes necessary to determine the Wobbe index, which is the heating value divided by the square root of the density. Gases of equal Wobbe index have similar burning characteristics and can be interchanged with each other before delivery of fuel to a customer. The Wobbe index can be calculated from measurements of heating value and relative density.

There are many other uses for the relative density in commerce in addition to these. The present invention is a novel method for measuring relative density that has important advantages over the state of the art.

Previous methods of measuring relative density can be divided into two categories. In the first category are those methods in which a known volume of the gas is actually weighed and compared to the weight of an equal volume of air. These methods have the disadvantage of requiring expensive equipment for precise weight measurement and also precisely controlling the pressure in this fixed volume. The pressure will determine the amount of gas that is weighed during each measurement; so it must be fixed.

The second category of methods are those in which a physical effect is used that depends on gas density. The magnitude of the effect in the unknown gas is compared to that in air. One method in this category measures the vibration frequency of a tuning fork or beam that is suspended in the gas.

A particularly simple physical effect that can be accurately measured is the flow of the gas through an orifice at a fixed pressure drop. In the orifices commonly used in flow measurement this flow depends not only on the density but also on a discharge coefficient that varies with Reynolds number. Well known graphs that give the discharge coefficient as a function of orifice design and Reynolds number are published in standard engineering texts and handbooks. With density changes of 2:1 it is possible under some conditions for the discharge coefficient to vary by 20% or more at the same flow. The orifices used for gas flow measurement are thus not satisfactory for accurately measuring relative density because of the complexities introduced by the presence of this additional variable in the relationship.

Gas flow measurements are usually carried out using orifice diameters that are 0.2 to 0.75 of the pipe diameter. Pressure drops across the orifice are measured in inches of water. Under these conditions, the flow is considered adiabatic through the orifice. There will, however, be temperature changes and other difficult-to-analyze effects and it is these which have been empirically collected together in the "discharge coefficient" for engineering design purposes.

I have discovered that by using a very small orifice or pore different flow conditions are established. Surprisingly, the varying discharge coefficient is no longer observed, and the elimination of this variable makes it possible to measure relative density as a simple (inverse square) function of flow rate.

BRIEF DESCRIPTION OF INVENTION

In accordance with the invention, gas under pressure is vented through a special plug in the flow line normally to atmospheric pressure. This plug contains one or more very small orifices in parallel. The apparatus measures the gas flow through the plug at fixed pressures. When properly designed, I have found that the square of the gas flow is inversely proportional to relative density for ideal gases.

In its broader method aspects, the present invention provides a measurement of the relative density including the steps of flowing the gas through an orifice in a line, measuring the pressure drop of the gas through the orifice, and calculating the flow rate of said gas therefrom. The orifice is sized with respect to the applied pressure causing the flow therethrough so that deviations from ideal gas behavior of the flowing gases, that is, supercompressibility effects, tend to be balanced by other flow effects, postulated to be Joule-Thompson effects, thus rendering an orifice discharge coefficient unnecessary in calculating flow rate from said pressure drop. The square of the so-calculated flow rate is inversely proportioned to the sought after parameter, the relative density. The proportionality factor may be established by calibrating with a standard gas of known relative density.

In another method aspect the present invention provides a measurement of relative density by using the flow rate determination method described and claimed in my U.S. Pat. No. 4,285,245 issued Aug. 25, 1981, that is, by flowing gas through an orifice in a line; periodically restricting or interrupting the flow of said gas at a point in said line upstream from the orifice; measuring the fall of pressure in said line with respect to time to obtain the flow rate through the orifice; and calculating the relative density, which is inversely proportional to the square of the flow rate, the orifice again being sized with respect to the applied pressure causing flow through it so that deviations from ideal behavior of the flowing gas are substantially balanced by other flow effects, thus rendering an orifice discharge coefficient unnecessary in calculating density.

From the foregoing it can be seen that the primary object of the present invention is the provision of methods and means for simply and effectively measuring the relative density of a gas. The manner in which this object, together with other objects and purposes, is attained may best be understood by considering the detailed description which follows, together with the accompanying drawing.

DESCRIPTION OF THE DRAWINGS

The single FIGURE of the drawing is a diagramatic flow diagram of an apparatus constructed in accordance with the invention for practicing the methods of the invention.

DESCRIPTION OF THE PREFERRED EMBODIMENT

In the drawing the apparatus of the invention is designated generally as 10. It includes a main flow line 11, which contains a plug 12 having a pore or orifice 13 therethrough. Preferably the line 11 includes a reservoir or enlargement 14 upstream of the orifice. Reservoir 14, in addition to providing a desired inertia or capacitance for the system, is desirably arranged to provide for good and efficient heat exchange with the environment.

Main flow line 11 is provided with pressure transducers 15 and 16, located upstream and downstream, respectively, of orifice 13. Calculating equipment, indicated at 17, is provided for electrically subtracting the pressure at 16 from that at 15 and for performing other arithmetic and control functions.

Gas is delivered to main flow line 11 through one of two feed lines 18, 19, each of which is provided with an electrically operated valve 20, 21. One feed line may be used to deliver the gas of interest to main line 11, and the other to deliver a calibrating or standardizing gas.

In operation one or the other of values 20 and 21 is closed, and gas under pressure is flowed through the other to main line 11 (and reservoir 14). The gas flows through pore or orifice 13 and is ultimately vented to atmosphere, returned to a pipeline, burned in a burner or otherwise disposed of. Pressure is detected at transducers 15, and 16, and their difference, $\Delta \rho$, is electrically calculated and used to calculate flow rate, which is electrically squared and inverted at 17 to produce a signal proportional to $\rho$, the relative density.

In an alternate mode of operation the valve 20 or 21 through which the gas of interest is being fed is periodically closed, at least partially, and the rate of fall of pressure with respect to time at transducer 15 is utilized to yield the flow rate (being proportional thereto), which is again squared and inverted to yield a relative density signal.

Joule-Thompson expansion of the gas as with a porous plug. Joule-Thompson expansion is a well known physical process in which the pressure of the gas suddenly changes. It is to be contrasted with a variable expansion which takes place over a continuum of intermediate pressures.

In Joule-Thompson expansion of an ideal gas there is no temperature change. Also, since the orifice is very small the velocity of gas exiting from the orifice will be orders of magnitude greater than the velocity of gas upstream of the plug. The rate of momentum change across the orifice is VM, where M is the flow and V is the average gas velocity exiting from the orifice. This is equal to the force or $A * dP$, where A is the orifice area and dP is the pressure drop. If $\rho$ is the density, $M = V\rho$. Setting the rate of momentum change to the force gives $\rho = A\ dP/V*V$. V squared will be proportional to the square of the gas flow and thus relative density will be inversely proportional to the square of the gas flow at a substantially fixed pressure drop.

With a real gas there is some cooling of the gas during the Joule-Thompson expansion. This is believed to account for the deviation from ideal behavior in plots of flow versus pressure when experimental data is obtained for real gases. This deviation from ideal behavior is related to the same factors that determine supercompressibility and can be cancelled out. The experimental apparatus measures the flow at pressures above atmospheric and therefore contain a deviation from ideal behavior due to the supercompressibility of real gases. For a given size orifice, there is a pressure for which the deviations, being of different sign, effectively cancel. This is shown in the experimental data reported in Table 1. There the values of $x = (F*F*D)/dP$, where F is measured flow and D is relative density of known test gases, are shown for various pressures dP above ambient. It is evident from Table 1 that for this particular experiment the applied pressure range of 11 to 13 psig is optimum using 0.002″ orifices.

TABLE I

| $\Delta \rho$ (PSIG): | 25.00 | 23.00 | 21.00 | 19.00 | 17.00 | 15.00 | 13.00 | 11.00 | 9.00 | 7.00 | 5.00 | 3.00 |
|---|---|---|---|---|---|---|---|---|---|---|---|---|
| Relative Density of Sample Gases | | | | | | $\frac{\rho V^2}{\Delta P}$ | | | | | | |
| 1.000 | 39078 | 37454 | 36308 | 35260 | 34428 | 33906 | 33346 | 32864 | 32513 | 32040 | 31462 | 30720 |
|  | 38846 | 37606 | 36500 | 35540 | 34720 | 34078 | 33558 | 33070 | 32676 | 32147 | 31562 | 30776 |
|  | 38886 | 37596 | 36500 | 35596 | 34820 | 34104 | 33490 | 33114 | 32760 | 32074 | 31562 | 30801 |
|  | 38812 | 37464 | 36596 | 35512 | 34792 | 34146 | 33592 | 33038 | 32636 | 32186 | 31636 | 30706 |
|  | 38836 | 37642 | 36596 | 35558 | 34752 | 34082 | 33604 | 33168 | 32656 | 32205 | 31536 | 30727 |
| 0.640 | 36108 | 35066 | 34404 | 33888 | 33508 | 33160 | 32828 | 32596 | 32585 | 32431 | 32109 | 31824 |
|  | 38108 | 36796 | 35896 | 34978 | 34256 | 33778 | 33416 | 33226 | 33102 | 32924 | 32668 | 32205 |
|  | 37994 | 36736 | 35900 | 35016 | 34282 | 33832 | 33482 | 33304 | 33118 | 32956 | 32692 | 32159 |
|  | 38022 | 36812 | 35858 | 35070 | 34326 | 33764 | 33440 | 33094 | 33038 | 32848 | 32668 | 32178 |
| 0.593 | 35900 | 34798 | 34086 | 33378 | 32896 | 32577 | 32232 | 32190 | 32178 | 32117 | 32105 | 31964 |
|  | 37574 | 36496 | 35644 | 34720 | 34168 | 33592 | 33328 | 33192 | 33238 | 32964 | 32884 | 32620 |
|  | 37668 | 36546 | 35644 | 34756 | 34104 | 33730 | 33296 | 33148 | 33054 | 32976 | 33004 | 32664 |
|  | 37668 | 36550 | 35610 | 34766 | 34190 | 33676 | 33390 | 33148 | 33144 | 32980 | 32992 | 32684 |
| 0.677 | 39290 | 37914 | 37030 | 36002 | 35328 | 34888 | 34378 | 34322 | 34156 | 34108 | 34226 | 34178 |
|  | 37168 | 36176 | 35338 | 34466 | 34008 | 33730 | 33470 | 33382 | 33408 | 33474 | 33588 | 33600 |
|  | 37158 | 36036 | 35268 | 34356 | 33870 | 33528 | 33374 | 33184 | 33266 | 33436 | 33546 | 33630 |
|  | 37158 | 35996 | 35296 | 34512 | 33862 | 33274 | 33222 | 33340 | 33420 | 33592 | 33600 | 33600 |

In my experiments ¼″ and ⅛″ lines have been used. One or more very small orifices are provided in the plug in the line. An orifice diameter of 0.002 inches in a saphire jewel has been satisfactory. Several orifices in parallel may be used in order to make the flow greater.

The theory by which the present invention operates is not fully understood and I do not wish to be confined to any particular theory of operation, but I postulate that with this type of arrangement I am achieving a

What is claimed is:

1. A method for measuring the relative density of a gas comprising:

flowing said gas under an applied pressure through an orifice or pore in a line;

measuring the pressure drop in said gas; and calculating the flow rate of said gas from said measured pressure drop;

said orifice or pore being very small relative to said line and sized with respect to the applied pressure so that deviations from ideal behavior of said flowing gas are substantially balanced by other flow effects, thus rendering an orifice discharge coefficient unnecessary in calculationg flow rate form said measured pressure drop, the square of said flow rate being inversely proportional to said relative density.

2. A method for measuring the relative density of a gas comprising:

flowing said gas under an applied pressure through an orifice or pore in a line;

periodically restricting flow of said gas at a point in said line upstream from said orifice or pore;

measuring the fall of pressure in said line with respect to time to obtain the flow rate through said orifice or pore; and calculating said relative density, which is inversely proportional to the square of said flow rate;

said orifice or pore being very small relative to said line and sized with respect to the applied pressure so that deviations from ideal behavior of said flowing gas are substantially balanced by other flow effects, thus rendering an orifice discharge coefficient unnecessary in calculating relative density.

3. Apparatus for measuring the relative density of a gas comprising:

a flow line having an orifice or pore therein;

means for flowing said gas under an applied pressure through said orifice or pore;

means for measuring the pressure drop across said orifice;

means for calculating the flow rate of said gas based on said pressure drop;

said orifice or pore being very small relative to said flow line and sized with respect to the applied pressure so that deviations from ideal behavior of said flowing gas are substantially balanced by other flow effects, thus rendering an orifice discharge coefficient unnecessary in calculating flow rate from said measured pressure drop, the square of said flow rate being inversely proportional to said relative density.

4. A method in accordance with claim 1 in which said orifice or pore is about 0.002 inches in diameter.

5. A method in accordance with claim 4 in which said applied pressure is between about 11 and about 13 psig.

6. A method in accordance with claim 5 in which said line has a diameter between about $\frac{1}{4}$ inch and $\frac{1}{8}$ inch.

7. A method in accordance with claim 2 in which said orifice or pore is about 0.002 inches in diameter.

8. A method in accordance with claim 7 in which said applied pressure is between about 11 and about 13 psig.

9. A method in accordance with claim 8 in which said line has a diameter between about $\frac{1}{4}$ inch and $\frac{1}{8}$ inch.

10. An apparatus in accordance with claim 3 in which said orifice or pore is about 0.002 inches in diameter.

11. An apparatus in accordance with claim 10 in which said applied pressure is between about 11 and about 13 psig.

12. An apparatus in accordance with claim 11 in which said line has a diameter between about $\frac{1}{4}$ inch and $\frac{1}{8}$ inch.

13. A method for determining the relative density of a gas comprising:

flowing said gas under applied pressure through an orifice in a line to change its pressure to the extent that the gas deviates from ideal behavior due to supercompressibility of the gas; measuring the pressure drop in said gas;

sizing said orifice with respect to said line and to said applied pressure to achieve cooling effects that offset said deviations from ideal behavior; and calculating the density of said gas from said measured pressure drop without the necessity of considering an orifice discharge coefficient.

14. The method of claim 13 wherein said step of calculating includes the steps of calculating the flow rate from said measured pressure drop and then calculating said density.

15. A method for determining the relative density of a gas comprising:

flowing said gas under an applied pressure through an orifice in a line to change its pressure to the extent that the gas deviates from ideal behavior due to the supercompressibility of the gas;

periodically restricting flow of said gas at a point in said line upstream from said orifice;

measuring the pressure deviations in said line with respect to time;

sizing said orifice with respect to said line and to said applied pressure to achieve cooling effects that offset said deviation from ideal behavior; and calculating the density of said gas from said measured pressure deviations without the necessity of considering an orifice discharge coefficient.

16. The method of claim 15 wherein said step of calculating includes the steps of calculating the flow rate from said measured pressure drop and then calculating said density.

* * * * *